United States Patent
Kaneko

(10) Patent No.: US 9,692,993 B2
(45) Date of Patent: Jun. 27, 2017

(54) ILLUMINATION ESTIMATION DEVICE, ILLUMINATION ESTIMATION METHOD, AND STORAGE MEDIUM

(71) Applicant: NEC Corporation, Minato-ku, Tokyo (JP)

(72) Inventor: Eiji Kaneko, Tokyo (JP)

(73) Assignee: NEC CORPORATION, Tokyo (JP)

( * ) Notice: Subject to any disclaimer, the term of this patent is extended or adjusted under 35 U.S.C. 154(b) by 0 days.

(21) Appl. No.: 14/895,585

(22) PCT Filed: May 22, 2014

(86) PCT No.: PCT/JP2014/002683
§ 371 (c)(1),
(2) Date: Dec. 3, 2015

(87) PCT Pub. No.: WO2014/203453
PCT Pub. Date: Dec. 24, 2014

(65) Prior Publication Data
US 2016/0119558 A1 Apr. 28, 2016

(30) Foreign Application Priority Data
Jun. 19, 2013 (JP) .................................. 2013-128754

(51) Int. Cl.
*G06K 9/00* (2006.01)
*H04N 5/33* (2006.01)
(Continued)

(52) U.S. Cl.
CPC ............... *H04N 5/332* (2013.01); *G06T 7/90* (2017.01); *H04N 5/2256* (2013.01); *G01N 21/27* (2013.01); *G06T 2207/10024* (2013.01)

(58) Field of Classification Search
CPC ...... H04N 5/332; H04N 5/2256; G06T 7/408; G06T 2207/10024; G06T 7/90; G01N 21/27
(Continued)

(56) References Cited

U.S. PATENT DOCUMENTS 7,123,844 B2 * 10/2006 Myrick ..................... G01J 3/18
372/29.014
8,538,195 B2 * 9/2013 Robinson ............. G06K 9/0057
382/276
(Continued)

FOREIGN PATENT DOCUMENTS

| JP | 2001186540 A | 7/2001 |
| JP | 2003209856 A | 7/2003 |

(Continued)

OTHER PUBLICATIONS

Gudrun J. Klinker, Steven A. Shafer, Takeo Kanade, "A Physical Approach to Color Image Understanding", International journal of Computer Vision, 1990.
(Continued)

*Primary Examiner* — Kanjibhai Patel

(57) ABSTRACT

Illumination estimation device includes: target object area extraction unit which extracts an object area from a multi-spectral image, the object area being an area, including specular reflection, of an object; distribution characteristics estimation unit which estimates information representing a subspace that approximates a distribution of observation values in a spectral space, as distribution characteristics, the distribution characteristics being characteristics of a spreading manner of the observation values in the object area within the spectral space; dimension reduction unit which selects a distribution characteristic to be used from among the distribution characteristics estimated by the distribution characteristics estimation unit depending on the number of
(Continued)

dimensions to be reduced, the number of dimensions to be reduced being determined in advance by a light environment; and illumination estimation unit which estimates spectral characteristics of illumination based on the subspace information to be represented by the distribution characteristic selected by the dimension reduction unit.

10 Claims, 10 Drawing Sheets

(51) Int. Cl.
  *H04N 5/225* (2006.01)
  *G06T 7/90* (2017.01)
  *G01N 21/27* (2006.01)
(58) Field of Classification Search
  USPC .............................. 382/162; 48/164; 348/164
  See application file for complete search history.

(56) References Cited

U.S. PATENT DOCUMENTS

| | | | | |
|---|---|---|---|---|
| 8,644,911 | B1* | 2/2014 | Panasyuk | A61B 5/0075 600/473 |
| 2010/0042004 | A1* | 2/2010 | Dhawan | A61B 5/0059 600/476 |
| 2012/0183213 | A1* | 7/2012 | Robles-Kelly | G06K 9/00362 382/165 |
| 2014/0293091 | A1* | 10/2014 | Rhoads | G01J 3/513 348/234 |

FOREIGN PATENT DOCUMENTS

| | | |
|---|---|---|
| JP | 2005311581 A | 11/2005 |
| JP | 2011022044 A | 2/2011 |
| JP | 2012237609 A | 12/2012 |

OTHER PUBLICATIONS

Graham D. Finlayson, Gerald Schaefer, "Solving for Colour Constancy using a Constrained Dichromatic Reflection Model", International journal of Computer Vision, 2001.
R.E. Bird, C. Riordan, "Simple Solar Spectral Model for Direct and Diffuse Irradiance on Horizontal and Tilted Planes at the Earth's Surface for Cloudless Atmospheres", Journal of Applied Meteorology and Climatology, vol. 25, Issue 1, 1986.
Eiji Kaneko, "Daylight Spectrum Model under Weather Conditions from Clear Sky to Cloudy", IPSJ SIG Notes, 2012 (Helsel 24) Nendo . 1 [CD-ROM], Jul. 2, 2012 (Jul. 2, 2012) (received date), vol. 2012-CV1M-182, No. 32, pp. 1 to 6 cited in the Specification and ISR.
International Search Report for PCT Application No. PCT/JP2014/002683, mailed on Aug. 26, 2014.
English translation of Written opinion for PCT Application No. PCT/JP2014/002683.
Finlayson G D et al: "Convex and non-convex illuminant constraints for dichromatic colour constancy", Proceedings 2001 IEEE Conference on Computer Vision and Pattern Recognition. CVPR 2001. Kauai, Hawaii, Dec. 8-14, 2001, IEEE Computer Society, Los Alamitos, C, val. 1, Dec. 8, 2001, pp. 598-604.
Mark S. Drew: "Optimization approach to dichromatic images". Journal of Mathematical Imaging and Vision, Jun. 1993, vol. 3, Issue 2, pp. 187-203. Kluwer Academic Publishers, in The Netherlands.
Extended European Search Report for EP Application No. EP14814071.8 dated on Jan. 2, 2017.

* cited by examiner x : OBSERVATION VALUE $L_{CLOUDY}(\theta)$

× : OBSERVATION VALUE $L_{CLOUDY}(\theta)$
← : FIRST MAIN COMPONENT $L_1$
←− − : SECOND MAIN COMPONENT $L_2$
←·−·− : ILLUMINATION $I_S$
←·····  : DIFFUSE REFLECTION LIGHT $L_{obj\_s}$

— PRIOR ART —

X:OBSERVATION VALUE L($\theta$)

ILLUMINATION ESTIMATION DEVICE, ILLUMINATION ESTIMATION METHOD, AND STORAGE MEDIUM

This application is a National Stage Entry of PCT/2014/002683 filed on May 22, 2014, which claims priority from Japanese Patent Application 2013-128754 filed on Jun. 19, 2013, the contents of all of which are incorporated herein by reference, in their Entirety.

TECHNICAL FIELD

The present invention relates to an image processing technique, and more particularly, to an illumination estimation device, an illumination estimation method, and an illumination estimation program for estimating spectral characteristics of illumination from an image.

BACKGROUND ART

There is a method employing a multispectral image recorded with multi-wavelength light as a technique for grasping various pieces of information such as the kind, the material, and the state of an object in a captured scene with high precision. The behavior of light of each wavelength when the light is reflected on the surface of an object differs depending on the kind or the state of the object. Therefore, it is possible to grasp the kind or the state of an object by obtaining reflection characteristics of the object from observed spectra, which are observation values to be recorded at the respective pixels of the multispectral image.

However, it is difficult to accurately acquire object information from observed spectra. This is because observed spectra include characteristics of illumination light in addition to reflection characteristics of an object. Observed spectra to be recorded at the respective pixels of a multispectral image is a result obtained by capturing the light reflected on the surface of an object irradiated with illumination light by a sensor. Therefore, the observed spectra include characteristics of illumination light in addition to reflection characteristics of an object. The observed spectra vary by an influence of illumination light in the environment where illumination varies such as outdoors. It is impossible to accurately acquire object information even with use of the observed spectra as described above.

In order to accurately acquire object information, it is necessary to accurately acquire characteristics of illumination light at the time of capturing image, and to remove an influence of illumination at the time of capturing image from a multispectral image, in other words, to remove a portion representing characteristics of illumination light from the observed spectra. Hereinafter, characteristics of light expressed as a spectral configuration are referred to as spectral characteristics.

A method for directly measuring illumination light can be considered as one of the methods for acquiring spectral characteristics of illumination at the time of capturing image. In this method, however, it is necessary to configure a system, in which an image sensor and an illumination light measuring sensor are integrated, in addition to the necessity of separately installing a sensor for measuring illumination light. This method causes disadvantages such as a cost increase and system oversizing. Further, it is necessary to install the illumination light measuring sensor at the same place as where a measurement object is placed, or near the place where a measurement object is placed. Therefore, when the distance between a measurement object and an image sensor is far, as exemplified by ground observation from an airplane, the following drawbacks may occur. Specifically, it may be impossible to physically install an illumination light measuring sensor, or a large amount of labor or a large amount of cost may be required even if it is possible to install an illumination light measuring sensor.

In order to avoid these drawbacks, it is desired to estimate spectral characteristics of illumination only with use of information on an observed multispectral image.

There is a method employing information on a surface reflectance (spectral reflectance) of an object to be observed for each wavelength, as one of the methods for estimating spectral characteristics of illumination at the time of capturing image from multispectral image information (see e.g. PTL 1).

In the method described in PTL 1, a color temperature of illumination is estimated by correlating an area of illumination with points on a black body locus, and by calculating and optimizing the energy necessary for satisfying the following assumption while changing the color temperature. PTL 1 uses an assumption that a skin color area or a gray color area of an object is large within an observed scene. If the color temperature of illumination can be estimated, it is possible to estimate spectral characteristics of illumination light from the estimated color temperature.

In the method described in PTL 1, however, it is assumed that a spectral reflectance of an object to be observed can be expressed by using a model whose spectral reflectance is known, and spectral characteristics of illumination are estimated based on the assumption. Therefore, this method involves the following drawbacks. Specifically, a spectral reflectance of an object is a value unique to the object, which is determined by the material or a like property of the object. The value of spectral reflectance varies depending on an object to be observed. Therefore, the assumption that it is possible to express the spectral reflectance of an intended object to be observed by using a model whose spectral reflectance is known is not always useful. Thus, in the method based on the aforementioned assumption, it is not always possible to accurately estimate spectral characteristics of illumination with respect to an intended object to be observed.

In order to solve the aforementioned drawbacks, it is necessary to estimate spectral characteristics of illumination, without an assumption on a surface reflectance of an object. Several methods employing a dichromatic reflection model are proposed as the method for implementing the aforementioned idea (see e.g. NPL 1 and NPL 2).

CITATION LIST

Patent Literature

PTL 1: Japanese Laid-open Patent Publication No. 2003-209856

Non Patent Literature

NPL 1: Gudrun J. Klinker, Steven A. Shafer, Takeo Kanade, "A Physical Approach to Color Image Understanding", International journal of Computer Vision, 1990.

NPL 2: Graham D. Finlayson, Gerald Schaefer, "Solving for Colour Constancy using a Constrained Dichromatic Reflection Model", International journal of Computer Vision, 2001.

SUMMARY OF INVENTION

Technical Problem

A dichromatic reflection model is a model, in which reflected light from an object is expressed as the sum of two kinds of reflection components i.e. a specular reflection component and a diffuse reflection component.

The specular reflection component is a component of reflected light that is generated by specular reflection, which is a phenomenon that light is reflected on the interface between an object and a medium through which light is transmitted. By specular reflection, light having a large intensity is emitted in a direction in which the angle of incidence and the angle of reflection are equal to each other. Normally, the specular reflection component has the same spectral characteristics as incident light.

On the other hand, the diffuse reflection component is a component of reflected light that is generated by diffuse reflection, which is a phenomenon that light incident on an object is emitted to the outside of the object after having undergone complicated reflections within the object near the interface between the object and a medium through which light is transmitted. Absorption and scattering of wavelength components which differ among the objects are generated in the process of reflecting light within the object. Therefore, the diffuse reflection component has different spectral characteristics from those of incident light.

The following Eq. (1) is an example of an equation expressing a dichromatic reflection model. When observation values of reflected light from an object are expressed by using a dichromatic reflection model, the dichromatic reflection model is expressed by the following Eq. (1).

[Equation 1]

$$l(\lambda, \vec{\theta}) = m_s(\vec{\theta})i(\lambda) + m_b(\vec{\theta})l_{obj}(\lambda) \qquad \text{Eq. (1)}$$

In Eq. (1), $\lambda$ represents a wavelength. Further, $\theta$ with an arrow represents an angle vector having the angle of incidence, the angle of reflection, and the angle of phase as components (in the following, the vector is expressed as $\theta$ in the description other than the equations. The same notation is applied to the other vectors). Further, $m_s(\theta)$ represents the amount of specular reflection, and $m_b(\theta)$ represents the amount of diffuse reflection. Further, $i(\lambda)$ represents spectral characteristics of incident light, and $I_{obj}(\lambda)$ represents spectral characteristics of diffuse reflection light. In Eq. (1), the observation value $I(\lambda,\theta)$ is expressed as the sum of a specular reflection component "$m_s(\theta)i(\lambda)$" and a diffuse reflection component "$m_b(\theta)I_{obj}(\lambda)$".

For the following description, the vector in Eq. (1) is expressed by the following Eq. (2).

[Equation 2]

$$\vec{L}(\vec{\theta}) = m_s(\vec{\theta})\vec{I} + m_b(\vec{\theta})\vec{L}_{obj} \qquad \text{Eq. (2)}$$

When it is assumed that N wavelengths to be measured by a sensor are $\lambda_1, \ldots,$ and $\lambda_n$, $L(\theta)$, I, and $L_{obj}$ are respectively N-th order vectors having $I(\lambda,\theta)$, $i(\lambda)$, and $I_{obj}(\lambda)$ in Eq. (1) as components (where i=1, . . . , and N). In the following, unless otherwise specifically mentioned, all the vectors described in the present specification are N-th order vectors having the values at wavelengths $\lambda_1, \ldots,$ and $\lambda_n$ as components. Further, the N-th order vector space is called as a spectral space.

In the method described in NPL 1, when considering a distribution of observation values that follows a dichromatic reflection model in a three-dimensional spectral space constituted of intensity information on light of wavelengths corresponding to three colors of red, green, and blue, particularly, when it is assumed that observation values are distributed in a T-shape, spectral characteristics of illumination are estimated from observation values based on the aforementioned assumption.

For instance, there may be a case, in which a smooth surface object having isotropic reflection characteristics as represented by plastic is observed under a single light source. In this case, when the angle vector $\theta$ changes, the amount of diffuse reflection varies in the region where the amount of specular reflection is assumed to be zero. On the other hand, the amount of diffuse reflection hardly varies in the region where the amount of specular reflection is significant. Thus, the observation values are distributed in a T-shape in a three-dimensional color space as illustrated in FIG. 10.

FIG. 10 is a schematic diagram illustrating a distribution of observation values $L(\theta)$ in a three-dimensional color space, which is assumed in NPL 1. In the method described in NPL 1, a specular reflection component and a diffuse reflection component are separated from each other based on an assumption that observation values $L(\theta)$ are distributed in a T-shape in a three-dimensional color space. However, this assumption is not always useful in a condition other than the condition in which an object has isotropic reflection characteristics under a single light source. For instance, the amounts of the two reflection components simultaneously vary on an object having a complicated surface configuration such as a wavy water surface. In this case, observation values $L(\theta)$ are distributed on a two-dimensional plane where a vector I representing spectral characteristics of illumination, and a vector $L_{obj}$ representing spectral characteristics of diffuse reflection light exist. However, the distribution configuration of observation values $L(\theta)$ does not always have a T-shape. Therefore, in the method described in NPL 1, it is impossible to accurately separate a specular reflection component and a diffuse reflection component in a condition other than the condition in which a smooth surface object is observed, and it is impossible to estimate illumination.

NPL 2 discloses a method, in which spectral characteristics of illumination are estimated while avoiding the aforementioned problem on separation of reflection components. The method described in NPL 2 employs that a three-dimensional color space can be transformed into a space constituted of one-dimensional brightness and two-dimensional chromaticity. With use of this method, it is possible to express spectral characteristics at three wavelengths corresponding to red, green, and blue as points on a two-dimensional plane representing chromaticity (called as a chromaticity diagram). In the method described in NPL 2, it is assumed that observation values follow a dichromatic reflection model, and a distribution of observation values projected on a chromaticity diagram is approximated by a straight line. Further, in the method described in NPL 2, illumination is modeled into a curve on the chromaticity diagram. Obtaining an intersection point, on the chromaticity diagram, between the aforementioned straight line representing a distribution of observation values, and the curve representing an illumination model, makes it possible to estimate the chromaticity of illumination at the time of observation. The estimated chromaticity of illumination is output as information representing spectral characteristics of illumination at the time of observation.

In the method described in NPL 2, it is possible to obtain chromaticity information representing spectral characteristics of illumination at the time of observation, without separating a specular reflection component and a diffuse reflection component by assuming that observation values are approximated by a straight line on a chromaticity diagram.

However, a chromaticity diagram is a two-dimensional plane to be expressed based on a three-dimensional color space of red, green, and blue. In the chromaticity diagram, although it is possible to express spectral characteristics of light at three wavelengths corresponding to red, green, and blue, it is not possible to uniquely express spectral characteristics including multi-wavelength light information. Thus, in the method described in NPL 2, there is a problem that it is hard to estimate spectral characteristics of illumination by using a multispectral image including multi-wavelength information.

Further, in the method described in NPL 2, color distribution characteristics by diffuse reflection and specular reflection are approximated as a straight line on a chromaticity diagram by assuming that the model of observation values is a simple dichromatic reflection model. However, color distribution characteristics by diffuse reflection and specular reflection may not be approximated as a straight line on a chromaticity diagram depending on the light environment at the time of capturing image. In such a case, there is a problem that it may be impossible to accurately estimate spectral characteristics of illumination only by assuming that the model of observation values follows a simple dichromatic reflection model.

For instance, when an object to be observed is irradiated with indirect light (hereinafter, referred to as ambient light) that is reflected and scattered on a wall, a cloud, the sky, or the like in addition to the light that is directly emitted from a light source, and it is impossible to ignore the amount of irradiation of ambient light, the observation values may not always follow a simple dichromatic reflection model as described above. In this case, observation values are not linearly distributed on a chromaticity diagram. Therefore, it is difficult to estimate spectral characteristics of illumination by the method described in NPL 2.

The invention has been made in view of the above, and aims to provide an illumination estimation device, an illumination estimation method, and an illumination estimation program that enable to precisely estimate spectral characteristics of illumination from a multispectral image including multi-wavelength information, without restricting the light environment at the time of capturing image or restricting the surface configuration of an object.

Solution to Problem

An exemplary illumination estimation device according to the present invention includes: a target object area extraction unit which extracts an object area from a multispectral image, the object area being an area, including specular reflection, of an object; a distribution characteristics estimation unit which estimates information representing a subspace that approximates a distribution of observation values in a spectral space, as distribution characteristics, the distribution characteristics being characteristics of a spreading manner of the observation values in the object area within the spectral space; a dimension reduction unit which selects a distribution characteristic to be used from among the distribution characteristics estimated by the distribution characteristics estimation unit depending on the number of dimensions to be reduced, the number of dimensions to be reduced being determined in advance by a light environment; and an illumination estimation unit which estimates spectral characteristics of illumination based on the subspace information to be represented by the distribution characteristic selected by the dimension reduction unit.

An exemplary illumination estimation method according to the present invention includes: extracting an object area from a multispectral image, the object area being an area, including specular reflection, of an object; estimating information representing a subspace that approximates a distribution of observation values in a spectral space, as distribution characteristics, the distribution characteristics being characteristics of a spreading manner of the observation values in the object area within the spectral space; selecting a distribution characteristic to be used from among the estimated distribution characteristics depending on the number of dimensions to be reduced, the number of dimensions to be reduced being determined in advance by a light environment; and estimating spectral characteristics of illumination based on the subspace information to be represented by the selected distribution characteristic.

An exemplary non-transitory computer readable storage medium recording thereon a program according to the present invention causes a computer to execute: a processing of extracting an object area from a multispectral image, the object area being an area, including specular reflection, of an object; a processing of estimating information representing a subspace that approximates a distribution of observation values in a spectral space, as distribution characteristics, the distribution characteristics being characteristics of a spreading manner of the observation values in the object area within the spectral space; a processing of selecting a distribution characteristic to be used from among the distribution characteristics estimated in the processing of estimating the information depending on the number of dimensions to be reduced, the number of dimensions to be reduced being determined in advance by a light environment; and a processing of estimating spectral characteristics of illumination based on the subspace information to be represented by the distribution characteristic selected in the prcessing of selecting.

Advantageous Effects of Invention

The present invention enables to estimate spectral characteristics of illumination from a multispectral image including multi-wavelength information, without restricting the light environment at the time of capturing image or restricting the surface configuration of an object. For instance, even when illumination includes ambient light, or even when the surface of an object to be observed is not smooth, it is possible to precisely estimate spectral characteristics of illumination from a multispectral image including multi-wavelength information.

DESCRIPTION OF EMBODIMENTS

First Exemplary Embodiment

Figure 1:
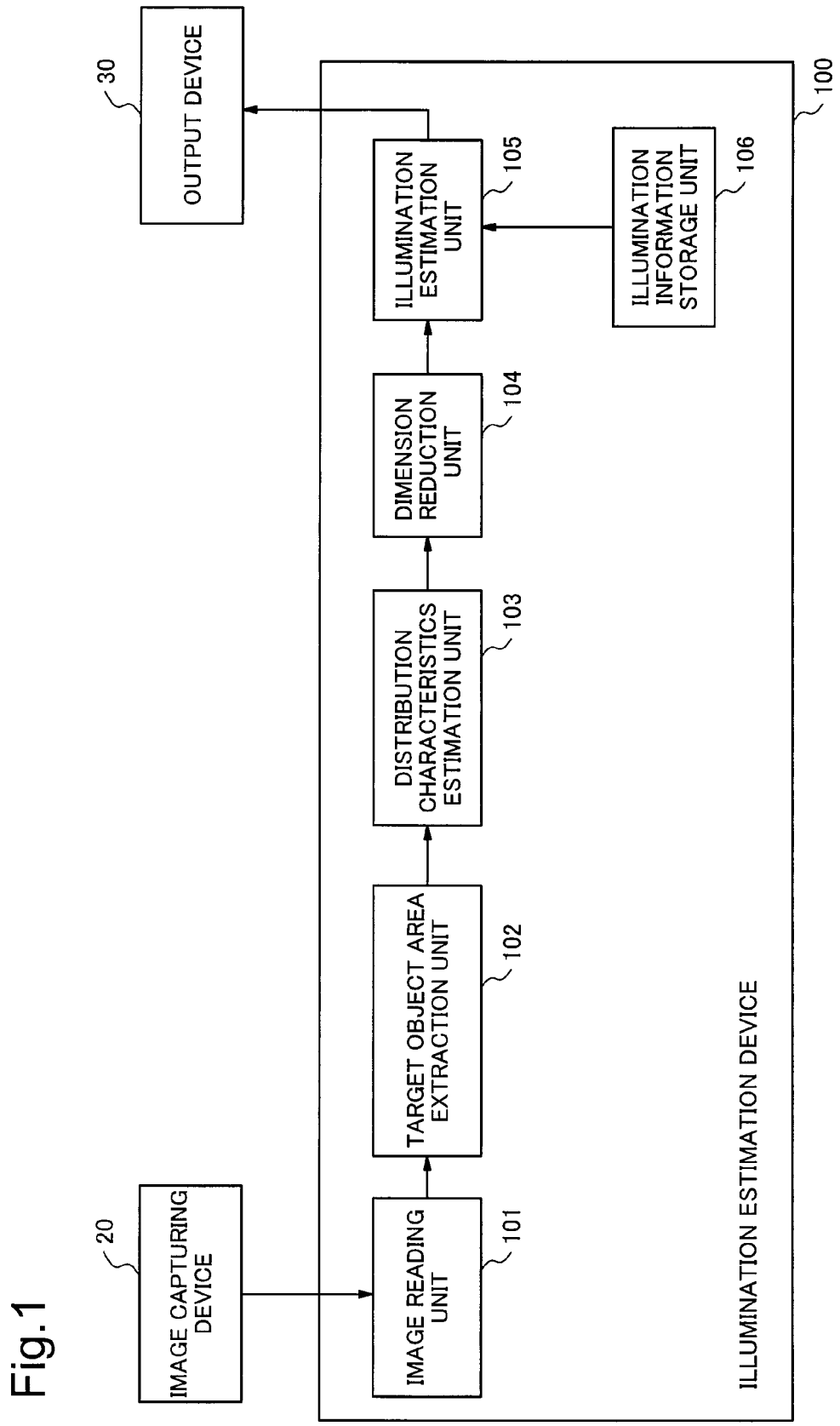
FIG. 1 is a block diagram illustrating a configuration example of an illumination estimation device in a first exemplary embodiment.

In the following, an exemplary embodiment of the invention is described referring to the drawings. FIG. 1 is a block diagram illustrating a configuration example of an illumination estimation device in the first exemplary embodiment of the invention. An illumination estimation device 100 illustrated in FIG. 1 includes an image reading unit 101, a target object area extraction unit 102, a distribution characteristics estimation unit 103, a dimension reduction unit 104, an illumination estimation unit 105, and an illumination information storage unit 106.

The image reading unit 101 reads an image captured by an image capturing device 20.

The target object area extraction unit 102 extracts an area including a specular reflection component of an object (hereinafter, referred to as an object area) from the image read by the image reading unit 101. It is possible to use an existing method as the object area extraction method.

The distribution characteristics estimation unit 103 estimates characteristics of the spreading manner of observation values in a spectral space, as distribution characteristics, based on observation values to be obtained from the respective pixels in an object area, which is extracted by the target object area extraction unit 102. For instance, when observation values have a distribution in the N-dimensional spectral space, the distribution characteristics estimation unit 103 may extract, as distribution characteristics, feature vectors constituting a subspace for each dimension, which is obtained by approximating a distribution of observation values in the spectral space to the subspace. Further, the distribution characteristics estimation unit 103 may extract main component vectors in a set of observation values, as distribution characteristics, for instance. Further, in outputting distribution characteristics, the distribution characteristics estimation unit 103 may rearrange feature vectors or main component vectors for each dimension, which are extracted as the distribution characteristics, in the descending order of eigenvalues for output.

The dimension reduction unit 104 selects a distribution characteristic to be used from among the distribution characteristics extracted by the distribution characteristics estimation unit 103 depending on the number of dimensions to be reduced, which is determined by the light environment. The dimension reduction unit 104 thus determines the dimension of a subspace that approximates a distribution of observation values in a spectral space.

The illumination information storage unit 106 stores information necessary for configuring an illumination model to be used by the illumination estimation unit 105. For instance, the illumination information storage unit 106 stores parameters and the like for use in an illumination model. The illumination model is not specifically limited. Preferably, however, the illumination model may be a model that expresses spectral characteristics of illumination based on a physical quantity that does not depend on an object to be observed such as a correlated color temperature.

The illumination estimation unit 105 estimates spectral characteristics of illumination at the time of capturing image, with use of a subspace to be defined by the reduced number of dimensions, which is represented by the distribution characteristic selected by the dimension reduction unit 104, and with use of an illumination model configured based on the information stored in the illumination information storage unit 106. The estimated spectral characteristics are output via an output device 30, for instance.

In the exemplary embodiment, the image reading unit 101, the target object area extraction unit 102, the distribution characteristics estimation unit 103, the dimension reduction unit 104, and the illumination estimation unit 105 are implemented by a CPU which operates according to a program, for instance. Further, the illumination information storage unit 106 is implemented by a storage device, for instance.

For instance, the illumination estimation device 100 may be an information processing device provided with a CPU (Central Processing Unit) which operates according to a program, various types of storage devices (such as a hard disk drive, a non-volatile memory, a volatile memory, and an SSD (Solid State Drive)), and a communication interface between the image capturing device 20 and the output device 30. FIG. 1 illustrates the illumination estimation device 100, the image capturing device 20, and the output device 30 as separate devices. Alternatively, the illumination estimation device 100 may be provided with the image capturing device 20 and the output device 30, or may be provided with one of the image capturing device 20 and the output device 30. Although FIG. 1 illustrates a configuration such that one device is provided with the image reading unit 101, the target object area extraction unit 102, the distribution characteristics estimation unit 103, the dimension reduction unit 104, and the illumination estimation unit 105, a part of these units may be implemented in another information processing device. In this case, the information processing devices are communicatively connected to each other.

Figure 2:
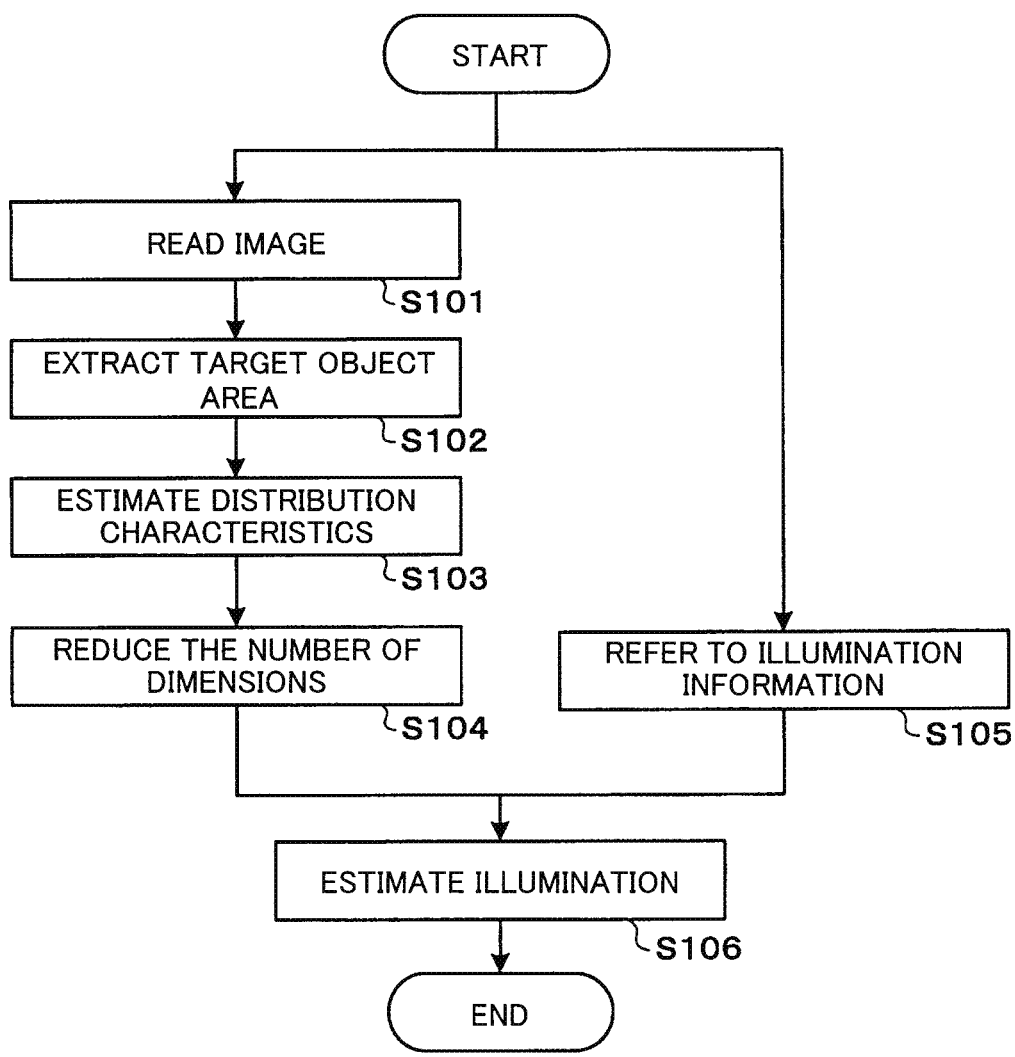
FIG. 2 is a flowchart illustrating an example of an operation to be performed by the illumination estimation device in the first exemplary embodiment.

FIG. 2 is a flowchart illustrating an example of an operation to be performed by the illumination estimation device 100 in the exemplary embodiment. In the example illustrated in FIG. 2, the image reading unit 101 reads an image captured by the image capturing device 20 (Step S101). The target object area extraction unit 102 extracts an object area including a specular reflection component from the image read by the image reading unit 101 (Step S102).

The distribution characteristics estimation unit 103 estimates characteristics of the spreading manner of observation values in a spectral space, as distribution characteristics, based on observation values to be obtained from the object area, which is extracted by the target object area extraction unit 102 (Step S103).

The dimension reduction unit 104 selects a distribution characteristic to be used from among the distribution characteristics estimated by the distribution characteristics estimation unit 103 depending on the number of dimensions to be reduced, which is determined by the light environment (Step S104).

The illumination estimation unit 105 reads the information stored in the illumination information storage unit 106, and configures an illumination model (Step S105). The operation of Step S105 may be performed in advance, or may be concurrently performed with the aforementioned operation.

The illumination estimation unit 105 estimates spectral characteristics of illumination, with use of a subspace which is represented by the distribution characteristic selected by the dimension reduction unit 104, and with use of the illumination model configured based on the information stored in the illumination information storage unit 106 (Step S106).

In the following, an operation of the exemplary embodiment is described using a practical example.

For instance, when capturing an image of a complicated surface configuration such as a wavy water surface, the amount of specular reflection and the amount of diffuse reflection of the reflected light from the object simultaneously vary. As a result, it is assumed that observation values have a distribution of an intended shape on a two-dimensional plane where the vector I representing spectral characteristics of illumination, and the vector $L_{obj}$ representing spectral characteristics of diffuse reflection light exist.

In the following, there is described an example, in which spectral characteristics of illumination are precisely estimated in an environment where the aforementioned observed spectra are obtained, even when the wavelengths to be observed from a captured multispectral image are not three wavelengths corresponding to red, green, and blue. Further, there is also described an example, in which spectral characteristics of illumination are precisely estimated from a captured multispectral image, even in a condition where ambient light included in illumination is not negligible such as an outdoor environment during the description of the aforementioned example.

In this example, the distribution characteristics estimation unit 103 extracts characteristics of the spreading manner of observation values in the N-dimensional space, with use of observation values to be obtained from a target object area including a specular reflection component. For instance, the distribution characteristics estimation unit 103 extracts feature vectors $v_1, v_2, \ldots,$ and $v_N$ which include the origin, and which constitute a space where observation values are distributed, based on an assumption that observation values are distributed in a space including the origin.

These vectors can be calculated based on a set of observation values and expressed as eigenvectors of $XX^T$, when a set of observation values constituted of N wavelengths at M pixels belonging to a target object area is expressed as a matrix X of N-rows and M-columns.

In addition to the above, as expressed by the following Eq. (3), when it is assumed that vectors $v_1, v_2, \ldots,$ and $v_N$ are arranged in the descending order of eigenvalues $\gamma_1, \gamma_2, \ldots,$ and $\gamma_N$ which give these eigenvectors, the feature vector clearly expresses the characteristics of the spreading manner of observation values, as the value of index decreases.

[Equation 3]

$$(\gamma_1 \vec{d} - XX^T)\vec{v}_1 = 0,$$

$$(\gamma_2 \vec{d} - XX^T)\vec{v}_2 = 0,$$

$$(\gamma_N \vec{d} - XX^T)\vec{v}_N = 0,$$

$$\gamma_1 > \gamma_2 > \ldots > \gamma_N \qquad \text{Eq. (3)}$$

Note that d represents a unit vector of N dimensions. Any solution method for solving the eigenvalue problem may be used as a method for obtaining $\gamma_i$ (i=1, . . . , and N) and $v_i$ (i=1, . . . , and N) from the matrix X. For instance, it is possible to solve the eigenvalue problem using a QR method.

As a method other than the above, for instance, the distribution characteristics estimation unit 103 may perform a main component analysis with respect to a set X of observation values, and may set the first main component vector, the second main component vector, . . . , and the N-th main component vector obtained by the analysis in order, as feature vectors $v_1, v_2, \ldots,$ and $v_N$.

The dimension reduction unit 104 selects a feature vector to be used from among the feature vectors $v_1, v_2, \ldots,$ and $v_N$ which constitute a space that approximates a distribution of observation values, which is estimated to be distribution characteristics by the distribution characteristics estimation unit 103, depending on the number P of dimensions to be reduced, which is determined by the expected light environment. In this example, the feature vectors $v_1, v_2, \ldots,$ and $v_P$ are selected in the order in which the characteristics of the spreading manner of observation values are clearly expressed, based on an assumption that feature vectors of dimensions up to the dimension number P are used.

The number P of dimensions to be reduced is determined to be the number of dimensions of a subspace that clearly expresses a distribution of observation values depending on the light environment at the time of capturing image within a spectral space, more specifically, is determined to be the same value as the number of vector components constituting an observation model depending on the light environment. In the following example, the observation model is a model based on a dichromatic reflection model. Specifically, the model that expresses observation values with use of two kinds of reflection components i.e. a specular reflection component and a diffuse reflection component is used as exemplified by a dichromatic reflection model. In this observation model, unlike the dichromatic reflection model described in NPL 1, however, reflection by ambient light is also considered as reflected light. The observation model to be used in the exemplary embodiment may not necessarily be a model based on a dichromatic reflection model, as far as the model expresses observation values with use of a component capable of specifying at least spectral characteristics of illumination.

The number of vector components constituting an observation model differs depending on the light environment in which the observation model is supposed to be placed. For instance, the number of vector components constituting an observation model depends on the number of illumination light (including ambient light) having different spectral characteristics, or depends on the presence or absence of a specular reflection component and a diffuse reflection component on an object to be observed in the light environment. In view of the above, the number P of dimensions to be reduced may be determined by setting a plurality of light environments in advance, taking into consideration the number of illumination light, or taking into consideration the presence or absence of each of the reflection components, and may be determined for each of the light environments depending on the set contents. In this case, the number P of dimensions to be reduced can be set by allowing an operator who inputs an image to designate a light environment to be expected from the image. Further, the number P of dimensions to be reduced may be directly designated by the operator.

In any of the cases, it is assumed that an appropriate value from 1 to N is set for the number P of dimensions to be reduced depending on the light environment. The following two examples are examples regarding the number P of dimensions to be reduced depending on the light environment, and a distribution characteristic to be selected. For instance, when the light environment is supposed to be such that observation values are expressed by the dichromatic reflection model expressed by the above Eq. (2), two feature vectors $v_1$ and $v_2$ are selected from among the distribution characteristics estimated by the distribution characteristics estimation unit 103, assuming that the number P of dimensions to be reduced is 2.

This is because in an observation model depending on the light environment in this example, in other words, in the model expressed by Eq. (2), observation values are distributed on a two-dimensional plane in the N-dimensional spectral space, which is constituted by two vector components i.e. spectral characteristics I of illumination and spectral characteristics $L_{obj}$ of reflected light from an object, and in which the two vectors exist. The illumination estimation unit 105 in the exemplary embodiment utilizes the characteristic that spectral characteristics I of illumination at the time of capturing image can be expressed as vectors on a two-dimensional plane where the feature vectors $v_1$ and $v_2$ exist.

Further, as another example, there is a light environment, in which illumination includes uniform ambient light from the sky, in other words, skylight, and the amount of skylight is not negligible. In the aforementioned light environment, four feature vectors $v_1$, $v_2$, $v_3$, and $v_4$ are selected from among the distribution characteristics estimated by the distribution characteristics estimation unit 103, assuming that the number P of dimensions to be reduced is 4. This is because, in this example, it is assumed that observation values include four vector components i.e. a specular reflection component I and a diffuse reflection component $L_{obj}$ of a light source, and a specular reflection component $I_s$ and a diffuse reflection component $L_{obj\_s}$ of skylight, and that observation values are distributed in a four-dimensional space where the four vectors exist within the N-dimensional spectral space. The illumination estimation unit 105 in the exemplary embodiment utilizes the characteristic that it is possible to express a specular reflection component I of a light source having the same spectral characteristics as the spectral characteristics of illumination at the time of capturing image, as vectors on a four-dimensional plane where the feature vectors $v_1$, $v_2$, $v_3$, and $v_4$ exist. With use of this method, it is possible to precisely estimate illumination even when ambient light included in illumination is not negligible. An example of an observation model depending on the light environment of this example is expressed by the following Eq. (4).

[Equation 4]

$$l(\lambda, \vec{\theta}) = m_s(\vec{\theta})\vec{I} + m_b(\vec{\theta})\vec{L}_{obj} + m_{ss}(\vec{\theta})\vec{I}_s + m_{sb}(\vec{\theta})\vec{L}_{obj\_s} \quad \text{Eq. (4)}$$

In Eq. (4), $m_{ss}(\theta)$ and $m_{sb}(\theta)$ respectively represent the amount of specular reflection and the amount of diffuse reflection of skylight. Further, $I_s$ and $L_{obj\_s}$ respectively represent a specular reflection component and a diffuse reflection component of skylight.

The illumination information storage unit 106 stores information necessary for configuring an illumination model. For instance, in a daylight model defined by the CIE (Commission Internationale de l'Eclairage), spectral characteristics of daylight are determined based on a correlated color temperature $T_C$. In the illumination model, as expressed by the following Eq. (5), spectral characteristics of daylight are expressed as a linear sum of an average vector $S_0$, a first main component vector $S_1$, and a second main component vector $S_2$, which are obtained from a database observed outdoors.

[Equation 5]

$$\vec{I}_{CIE}(T_c) = \vec{S}_0 + M_1(T_c)\vec{S}_1 + M_2(T_c)\vec{S}_2 \quad \text{Eq. (5)}$$

Weight coefficients $M_1$ and $M_2$ of the main component vectors in Eq. (5) are determined by a function using a correlated color temperature $T_C$ as an input. For instance, when the model is used as an illumination model, the illumination information storage unit 106 may store functional parameters for use in calculating the weight coefficients $M_1$ and $M_2$ from the average vector $S_0$, the first main component vector $S_1$, the second main component vector $S_2$, and the correlated color temperature $T_C$, as illumination information.

In such a case, the illumination estimation unit 105 may select an illumination condition, which is most analogous to a subspace that approximates a distribution of observation values to be represented by the selected feature vectors, from the illumination model to be configured based on the information stored in the illumination information storage unit 106, and may set spectral characteristics $I_{est}$ of illumination to be specified by the illumination condition, as an estimated value.

Figure 3:
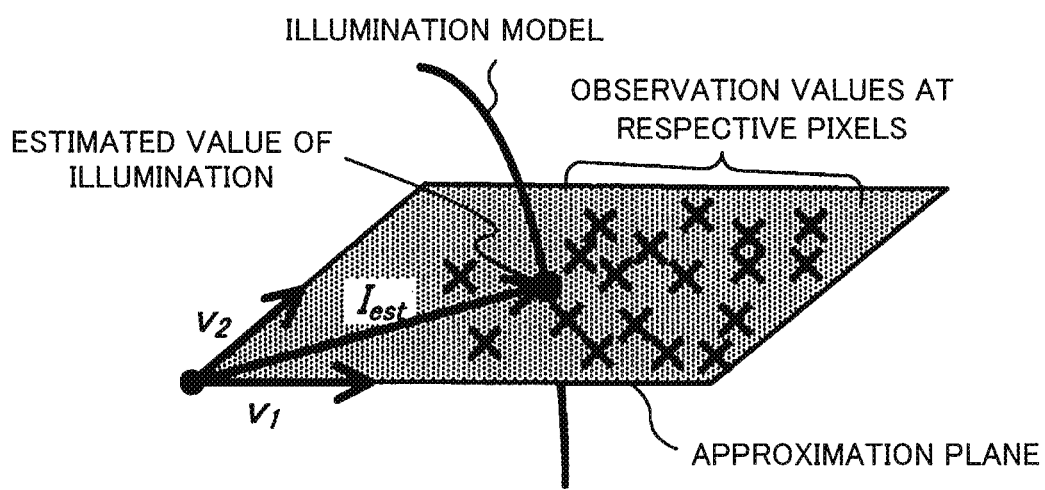
FIG. 3 is a conceptual diagram illustrating an illumination estimation method in the first exemplary embodiment.

FIG. 3 is a conceptual diagram illustrating an illumination estimation method in the exemplary embodiment. FIG. 3 illustrates a conceptual diagram of an illumination estimation method to be used when two vectors $v_1$ and $v_2$ are selected as feature vectors, which constitute a subspace that approximates observation values. As illustrated in FIG. 3, the illumination estimation unit 105 may set the intersection point between a two-dimensional plane where the feature vectors $v_1$ and $v_2$ exist in a spectral space, and an approximation curve of illumination expressed by an illumination model in a spectral space, as an estimated value of illumination.

The following is a practical example of a method for estimating spectral characteristics of illumination when the CIE daylight model expressed by Eq. (5) is given as the illumination model. In this case, solving the estimation problem on illumination is the same as solving the problem expressed by the following Eq. (6). Specifically, it is possible to calculate an estimated value of illumination by repeatedly calculating a distance between spectral characteristics $I_{CIE}(T_C)$ of illumination expressed by the given CIE daylight model, and a vector space constituted of selected feature vectors as base vectors, while changing the correlated color temperature $T_C$, and by extracting spectral characteristics of daylight that minimizes the distance.

[Equation 6]

$$\vec{I}_{est} = \min_{\vec{I}_{CIE}(T_c)} \left( \vec{I}_{CIE}(T_c) - \sum_{i=1}^{P} a_i v_i \right)^2 \quad \text{Eq. (6)}$$

The term Σ in Eq. (6) represents vectors in the subspace, specifically, represents vectors which are most approximate to spectral characteristics $I_{CIE}(T_C)$ of illumination to be specified by the illumination model when a certain correlated color temperature $T_C$ is given. It is possible to derive the values of $a_1, a_2, \ldots,$ and $a_P$ that satisfy this condition by analytical solution. For instance, the values of $a_1, a_2, \ldots,$ and $a_P$ can be calculated as expressed by the following Eq. (7) when spectral characteristics $I_{CIE}(T_C)$ of illumination to be expressed by the CIE daylight model, and base vectors $v_1, v_2, \ldots,$ and $v_P$ are given.

[Equation 7]

$$\begin{bmatrix} a_1 \\ a_2 \\ \vdots \\ a_P \end{bmatrix} = (V^T V)^{-1} V^T \vec{I}_{CIE}(T_c) \quad \text{Eq. (7)}$$

where $$V = [\, v_1 \quad v_2 \quad \ldots \quad v_P \,]$$

The illumination model may be an illumination model other than the CIE daylight model. For instance, it is possible to use a physical model representing daylight by Bird et al., as described in "R. E. Bird, C. Riordan, "Simple Solar Spectral Model for Direct and Diffuse Irradiance on Horizontal and Tilted Planes at the Earth's Surface for Cloudless Atmospheres", Journal of Applied Meteorology and Climatology, Vol. 25, Issue 1, 1986." (NPL 3). In this model, direct sunlight and atmospheric scattering light are simulated with use of the zenith angle of the sun to be calculated from the place and the time, or with use of a parameter representing the state of the atmosphere for calculating daylight in a fine weather. When this model is used, firstly, prescribed values are set for the parameters which are less likely to affect a simulation result, and measurable parameters are given to the model. Next, selecting the daylight that minimizes the distance to the subspace where the base vectors $v_1, v_2, \ldots,$ and $v_p$ exist, while changing the rest of unknown parameters makes it possible to estimate spectral characteristics of illumination.

Further, it is also possible to use a daylight model for a cloudy weather by Kaneko et al., as described in "E. Kaneko, M. Toda, H. Aoki, M. Tsukada, "Daylight spectrum model under weather conditions from clear sky to cloudy", Pattern Recognition (ICPR), 2012." (NPL 4). In this model, daylight in a cloudy weather is expressed as a mixture of direct sunlight in a fine weather and atmospheric scattering light in a fine weather, and the mixing ratio is changed depending on the degree of cloudiness. When this model is used, selecting daylight that minimizes the distance to a subspace where the base vectors $v_1, v_2, \ldots,$ and $v_p$ exist, while changing the mixing ratio, makes it possible to estimate spectral characteristics of illumination.

As described above, according to the exemplary embodiment, it is possible to precisely estimate spectral characteristics of illumination from a multispectral image including multi-wavelength information, even when illumination includes ambient light or even when the surface configuration of an object to be observed is complicated. This is because, in the illumination estimation method in the exemplary embodiment, N feature vectors are estimated based on an assumption that the feature vectors represent characteristics (distribution characteristics) of the spreading manner of observation values in a state that a specular reflection component and a diffuse reflection component are included, and illumination is estimated from a subspace that approximates a distribution of observation values to be expressed by feature vectors by the amount corresponding to the reduced number of dimensions, out of the estimated feature vectors, and from the illumination model to be configured based on illumination information. Thus, it is possible to estimate illumination, while avoiding the problem on separation of a specular reflection component and a diffuse reflection component, which is difficult to be solved when illumination includes ambient light or when the surface configuration of an object to be observed is complicated.

Further, in the illumination estimation method in the exemplary embodiment, the distribution characteristics estimation unit 103 extracts distribution characteristics of observation values in a spectral space, and then, the dimension reduction unit 104 selects a distribution characteristic to be used depending on the number of dimensions to be reduced, which is determined by the light environment. Therefore, it is possible to estimate illumination based on projection of observation values onto a subspace of an intended variable dimensions depending on an input image, without using a fixed two-dimensional subspace such as a chromaticity plane. Thus, it is possible to estimate spectral characteristics of illumination with use of a subspace depending on an input image, without restricting the component of information (such as a wavelength) to be used, even if the input image is a multispectral image including multi-wavelength light information.

Second Exemplary Embodiment

Figure 4:
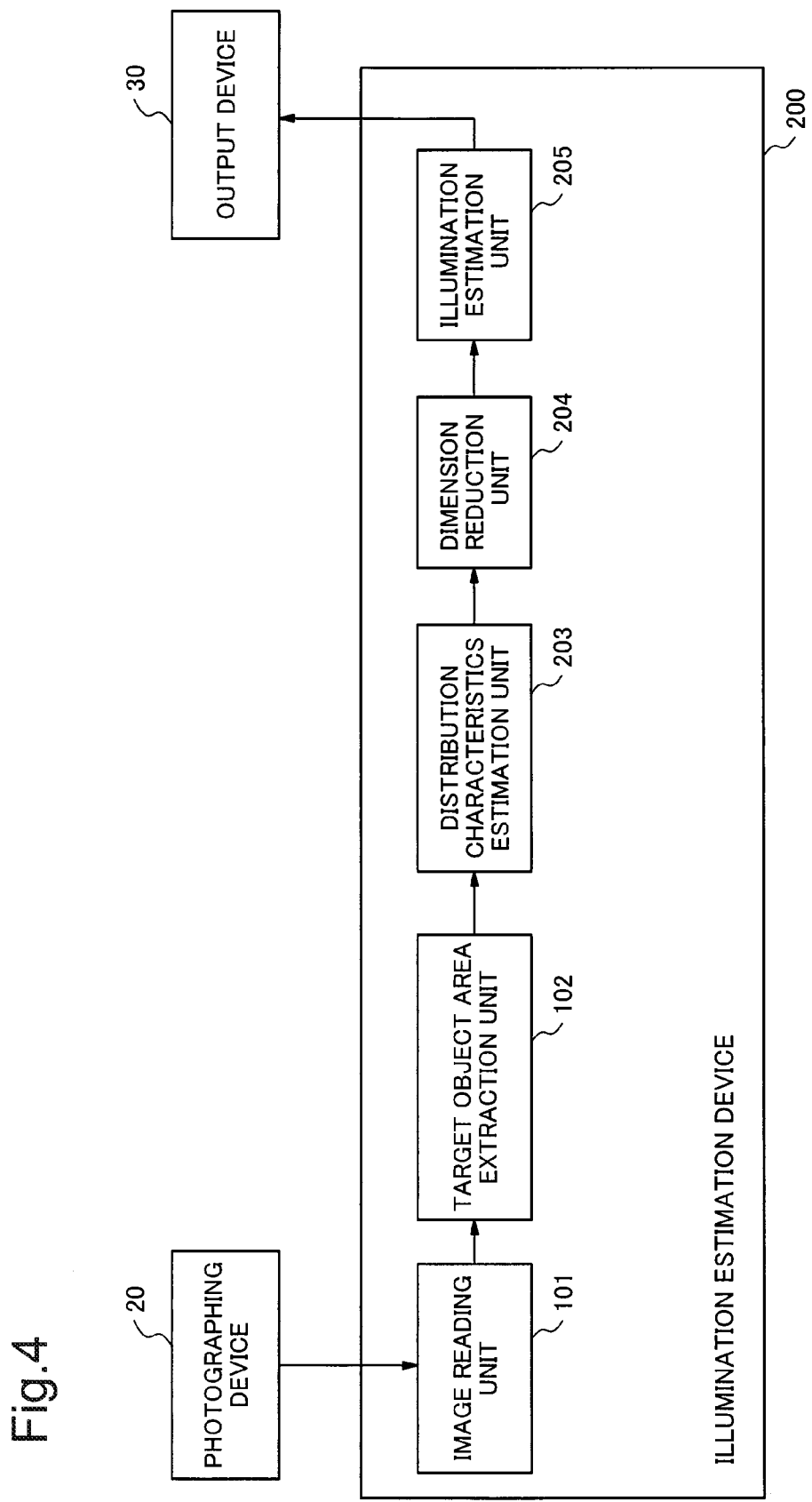
FIG. 4 is a block diagram illustrating a configuration example of an illumination estimation device in a second exemplary embodiment.

Next, the second exemplary embodiment of the invention is described. FIG. 4 is a block diagram illustrating a configuration example of an illumination estimation device in the second exemplary embodiment of the invention. An illumination estimation device 200 illustrated in FIG. 4 includes the image reading unit 101, the target object area extraction unit 102, a distribution characteristics estimation unit 203, a dimension reduction unit 204, and an illumination estimation unit 205. The image reading unit 101 and the target object area extraction unit 102 in the second exemplary embodiment may be the same as those in the first exemplary embodiment. Therefore, the image reading unit 101 and the target object area extraction unit 102 in the second exemplary embodiment are indicated with the same reference signs as those in the first exemplary embodiment, and description thereof is omitted herein. In addition, the illumination information storage unit 106 is not necessary in the exemplary embodiment.

The distribution characteristics estimation unit 203 estimates characteristics of the spreading manner of observation values in a spectral space, as distribution characteristics, based on observation values in an object area including a specular reflection component extracted by the target object area extraction unit 102.

The dimension reduction unit 204 selects a distribution characteristic to be used from among the distribution characteristics estimated by the distribution characteristics estimation unit 203 depending on the number of dimensions to be reduced, which is determined by the light environment.

The illumination estimation unit 205 estimates spectral characteristics of illumination with use of a subspace to be defined by the reduced number of dimensions, which is represented by the distribution characteristic selected by the dimension reduction unit 204. The illumination estimation unit 205 in the exemplary embodiment does not use an illumination model. The illumination estimation unit 205 estimates spectral characteristics of illumination from a distribution of observation values in a subspace, which is expressed by feature vectors selected by the dimension reduction unit 204.

Therefore, the dimension reduction unit 204 selects a distribution characteristic of such a dimension that a distribution of observation values in the subspace clearly expresses spectral characteristics of illumination included in the observation values.

The distribution characteristics estimation unit 203 extracts distribution characteristics in such a manner that at least the aforementioned dimension is included. As a practical method for implementing the above, a process of extracting distribution characteristics, a process of reducing the number of dimensions, and a process of estimating spectral characteristics of illumination may be executed according to respective predetermined methods, in the second exemplary embodiment as well as in the first exemplary embodiment.

Figure 5:
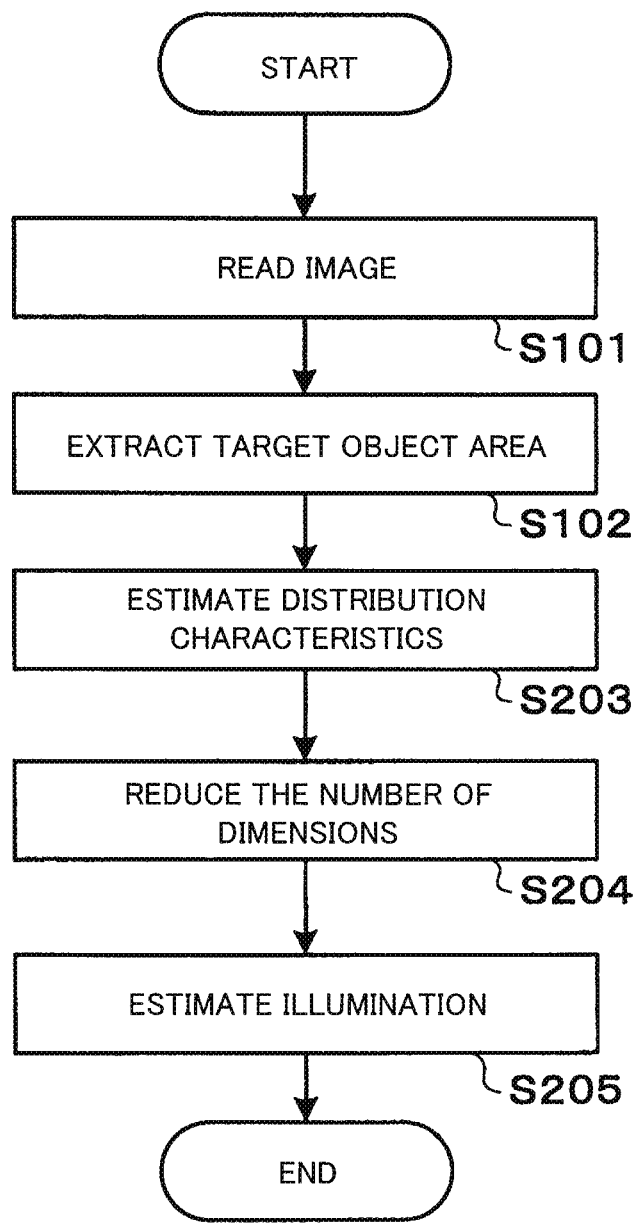
FIG. 5 is a flowchart illustrating an example of an operation to be performed by the illumination estimation device in the second exemplary embodiment.

FIG. 5 is a flowchart illustrating an example of an operation to be performed by the illumination estimation device 200 in the exemplary embodiment.

In the example illustrated in FIG. 5, as well as the first exemplary embodiment, the image reading unit 101 reads an image photographed by a image capturing device 20 (Step S101). Subsequently, the target object area extraction unit 102 extracts an object area including a specular reflection component from the image read by the image reading unit 101 (Step S102).

Subsequently, the distribution characteristics estimation unit 203 outputs, as distribution characteristics, characteristics of the spreading manner of observation values in a spectral space based on observation values in the object area including the specular reflection component, which is extracted by the target object area extraction unit 102 (Step S203).

Subsequently, the dimension reduction unit 204 selects a distribution characteristic to be used from among the distribution characteristics estimated by the distribution characteristics estimation unit 203 depending on the number of dimensions to be reduced, which is determined by the light environment (Step S204).

The illumination estimation unit 205 estimates spectral characteristics of illumination with use of the subspace, which is represented by the distribution characteristic selected by the dimension reduction unit 204 (Step S205).

In the following, an operation of the exemplary embodiment is described using a practical example. In the following, for the sake of description, it is assumed that observation values are obtained when a water surface is photographed outdoors in a cloudy weather, as a representative example when illumination includes only ambient light.

An example of a mathematical model of observation values in the aforementioned case is expressed by the following Eq. (8). In Eq. (8), $m_{ss}(\theta)$ represents the amount of specular reflection of ambient light from the sky, in other words, the amount of specular reflection of skylight, and $m_{sb}(\theta)$ represents the amount of diffuse reflection of skylight. Further, $I_s$ represents a specular reflection component of skylight, and $L_{obj\_s}$ represents a diffuse reflection component of skylight.

[Equation 8]

$$\vec{L}_{cloudy}(\vec{\theta}) = m_{ss}(\vec{\theta})\vec{I}_s + m_{sb}(\vec{\theta})\vec{L}_{obj\_s} \quad \text{Eq. (8)}$$

When photographed outdoors in a cloudy weather, since the sun is hidden behind the clouds, illumination light does not include direct sunlight from the sun as a light source. Therefore, a specular reflection component and a diffuse reflection component of direct sunlight can be ignored. Further, when it is assumed that in many water areas in the nature such as a sea surface or a lake surface, the ratio of the sky with respect to the expanse is large, and that the state of the sky is uniform, spectral characteristics of illumination become spectral characteristics of a specular reflection component $I_s$ of ambient light from the sky i.e. of skylight. On the basis of the aforementioned assumption, observation light on the water surface can be expressed as the sum of a specular reflection component $I_s$ of skylight and a diffuse reflection component $L_{obj\_s}$ of skylight, as expressed by Eq. (8). In particular, when an image of an object whose surface configuration is complicated such as a wavy water surface is photographed, it is assumed that the amount of two reflection components simultaneously vary, and as a result, observation values are distributed on a two-dimensional plane where two vectors exist.

Figure 6:
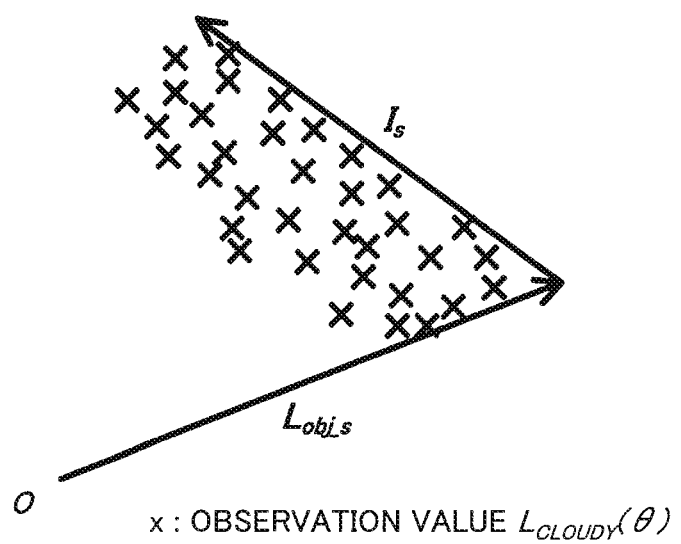
FIG. 6 is a conceptual diagram illustrating how observation values to be obtained from an image of a water surface captured outdoors in a cloudy weather are distributed in a spectral space.

FIG. 6 is a conceptual diagram illustrating the present case, in other words, how observation values to be obtained from an image of a water surface, which is photographed outdoors in a cloudy weather, are distributed in a spectral space. When the observation values are plotted in the N-dimensional space based on the aforementioned assumption, it is possible to approximate a distribution of observation values, with use of the two-dimensional plane as illustrated in FIG. 6. Further, in this case, the vector $I_s$ of skylight is a vector on the two-dimensional plane.

Figure 7:
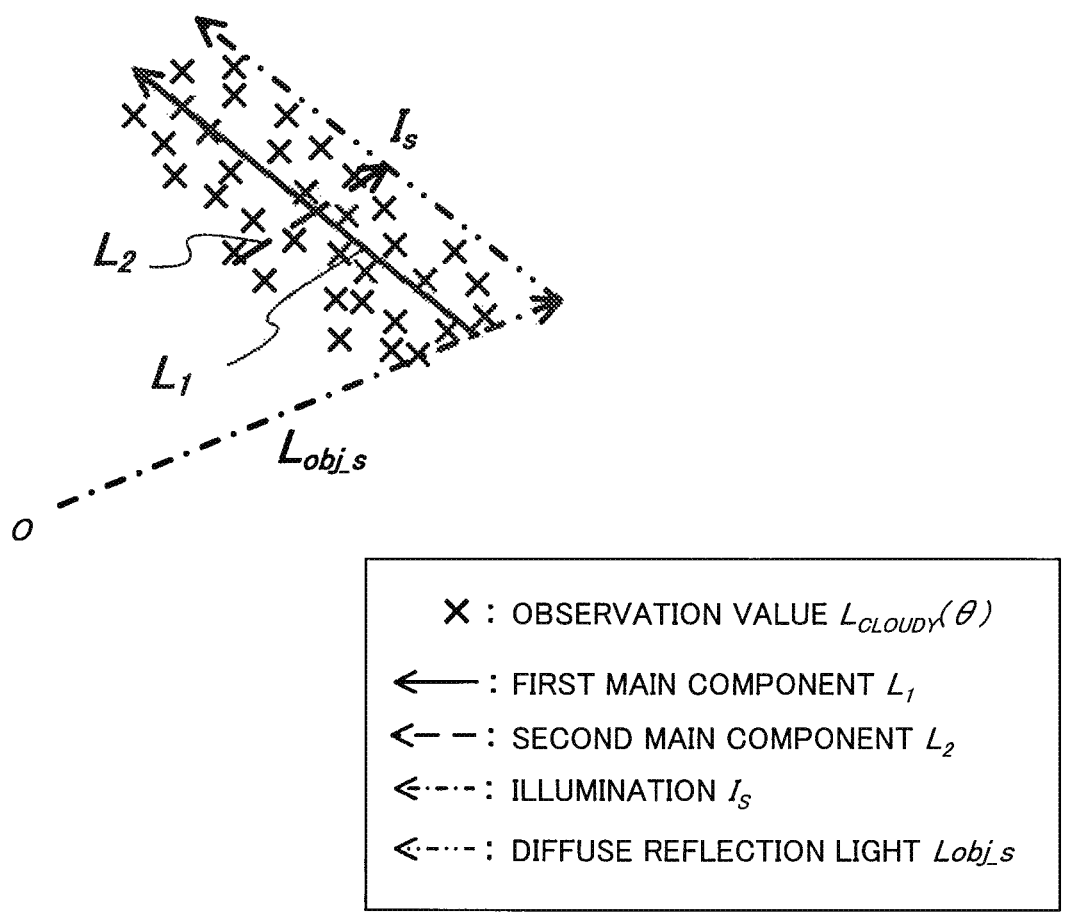
FIG. 7 is a conceptual diagram illustrating an example of a relationship between a distribution of observation values, and vectors representing distribution characteristics.
Figure 8:
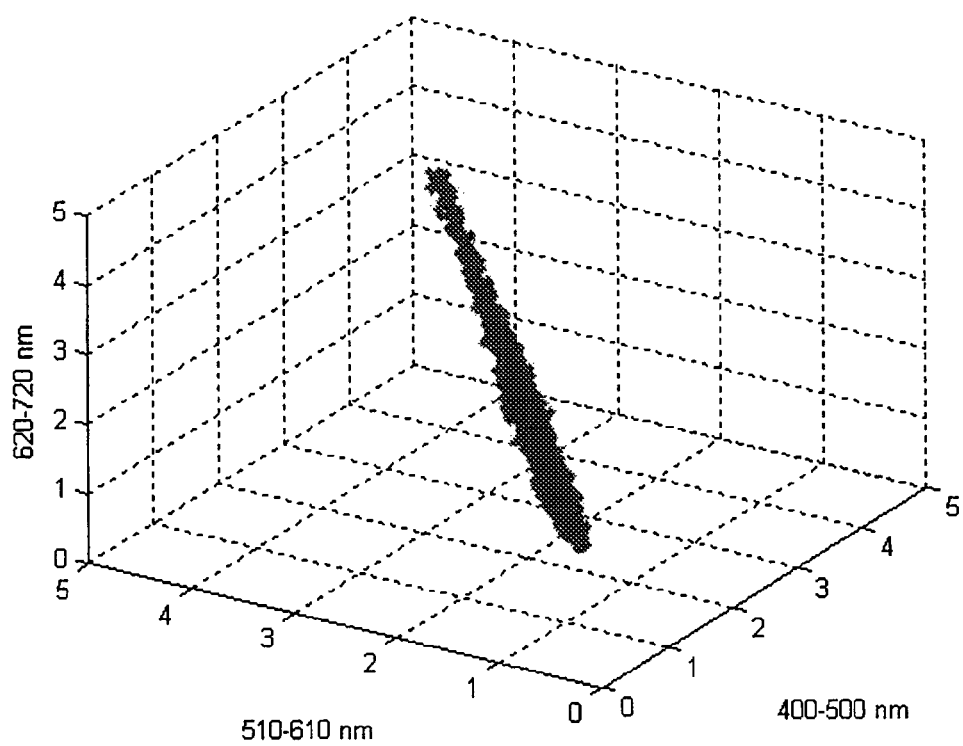
FIG. 8 is an explanatory diagram illustrating an example of a distribution of observation values when it is assumed that a wavelength is expressed as a dimension.

Observation values are likely to be widely distributed in the direction $I_s$ toward skylight especially in an environment such a cloudy weather. FIG. 7 is a conceptual diagram illustrating a relationship between a distribution of observation values, and vectors representing distribution characteristics in the present case. Further, FIG. 8 is an explanatory diagram illustrating an example of a distribution of observation values in the present case, when it is assumed that a wavelength is expressed as a dimension. The example illustrated in FIG. 8 is a distribution example of observation values when the amount of specular reflection greatly varies.

As illustrated in FIG. 7, in a case which is assumed in this example, a vector $L_1$ representing a direction in which the variation is largest is the first main component vector of observation value $L_{cloudy}(\theta)$, and is a vector in the same direction as the vector $I_s$ representing skylight. A vector whose direction is the same in a spectral space has the same spectral configuration. In other words, it is possible to estimate spectral characteristics of skylight i.e. of illumination by obtaining the first main component vector. In this example, spectral characteristics I of illumination are estimated with use of the aforementioned characteristics.

More specifically, when observation values on a wavy water surface where only skylight is illumination are input, the distribution characteristics estimation unit 203 in the exemplary embodiment estimates an average vector of the observation values, and the first to the N-th main component vectors $L_1, L_2, \ldots,$ and $L_N$, as information representing the characteristics of the spreading manner (variation) of observation values in a spectral space, in other words, distribution characteristics. The dimension reduction unit 204 extracts the first main component vector $L_1$ from among the vectors representing the distribution characteristics estimated by the distribution characteristics estimation unit 203. The illumination estimation unit 205 sets the vector $L_1$ extracted by the dimension reduction unit 204, as an estimated value of spectral characteristics $I_s$ of illumination.

As described above, according to the exemplary embodiment, it is possible to estimate spectral characteristics of illumination based on a multispectral image, which is photographed in a predetermined light environment and which includes multi-wavelength light information, without using an illumination model. This is because as well as in the first exemplary embodiment, observation values are projected onto a subspace of an intended variable number of dimensions depending on an input image, without using a fixed two-dimensional subspace such as a chromaticity plane, and thereby illumination is estimated based on the subspace.

Figure 9:
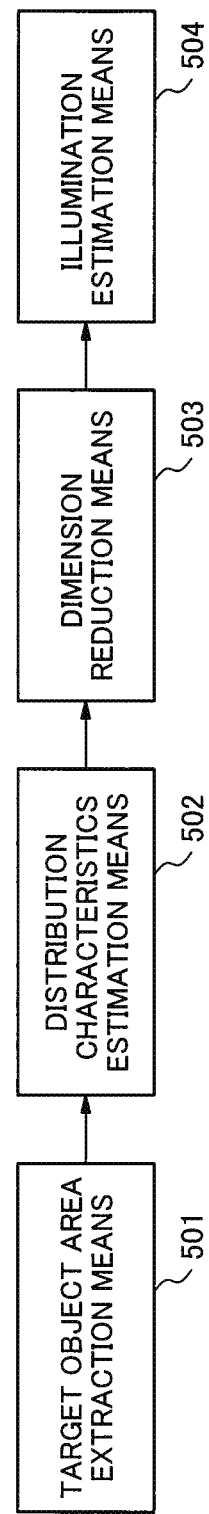
FIG. 9 is a block diagram illustrating a minimum configuration example of an illumination estimation device in the invention.
Figure 10:
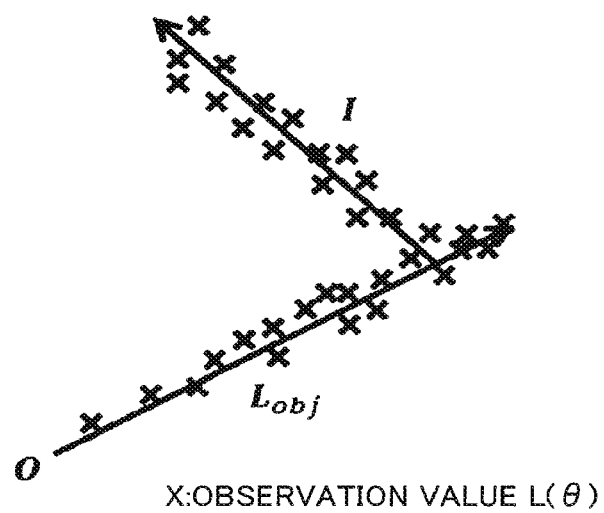
FIG. 10 is a schematic diagram illustrating a distribution of observation values in a three-dimensional color space, which is assumed in NPL 1.

Next, a minimum configuration of the illumination estimation device according to the invention is described. FIG. 9 is a block diagram illustrating a minimum configuration example of the illumination estimation device in the invention.

As illustrated in FIG. 9, the illumination estimation device in the invention includes, as minimum constituent elements, target object area extraction means 501, distribution characteristics estimation means 502, dimension reduction means 503, and illumination estimation means 504.

In the illumination estimation device having a minimum configuration illustrated in FIG. 9, the target object area extraction means 501 (e.g. the target object area extraction unit 102) extracts an object area, including specular reflection, of an object, from a multispectral image.

The distribution characteristics estimation means 502 (e.g. the distribution characteristics estimation unit 103, 203) estimates information representing a subspace that approximates a distribution of observation values in a spectral space, as distribution characteristics, which are characteristics of the spreading manner of observation values in the object area within a spectral space.

The dimension reduction means 503 (e.g. the dimension reduction unit 104, 204) selects a distribution characteristic to be used from among the distribution characteristics estimated by the distribution characteristics estimation means 502 depending on the number of dimensions to be reduced, which is determined in advance by the light environment.

The illumination estimation means 504 (e.g. the illumination estimation unit 105, 205) estimates spectral characteristics of illumination based on subspace information to be represented by the distribution characteristic selected by the dimension reduction means 503. Therefore, according to the illumination estimation device having a minimum configuration, spectral characteristics of illumination are estimated based on a subspace that approximates a distribution of observation values by the number of dimensions to be reduced depending on the light environment, wherein the distribution is particularly selected from among the estimated characteristics (distribution characteristics) of the spreading manner of observation values in the object area. Therefore, the illumination estimation device makes it possible to precisely estimate spectral characteristics of illumination from a multispectral image including multi-wavelength information, even when illumination includes ambient light or even when the surface configuration of an object to be observed is complicated.

Each of the exemplary embodiments as described above is a preferred exemplary embodiment of the invention. The scope of the invention is not limited only by the aforementioned exemplary embodiments. Various modified exemplary embodiments are implementable as far as such modified exemplary embodiments do not depart from the gist of the invention.

As is clear from the aforementioned description, it is possible to configure each component by hardware. Alternatively, each component may be implemented by a computer program. In this case, a processor which operates by a program stored in a program memory implements the same functions and operations as those of each of the aforementioned exemplary embodiments. Further, it is possible to implement only a part of the functions of the aforementioned exemplary embodiments by a computer program.

Further, a part or all of the exemplary embodiments may be described as the following Supplemental Notes. The invention, however, is not limited by the following.

(Supplemental Note 1)

An illumination estimation device, including:

target object area extraction means which extracts an object area from a multispectral image, the object area being an area, including specular reflection, of an object;

distribution characteristics estimation means which estimates information representing a subspace that approximates a distribution of observation values in a spectral space, as distribution characteristics, the distribution characteristics being characteristics of a spreading manner of the observation values in the object area within the spectral space;

dimension reduction means which selects a distribution characteristic to be used from among the distribution characteristics estimated by the distribution characteristics estimation means depending on the number of dimensions to be reduced, the number of dimensions to be reduced being determined in advance by a light environment; and illumination estimation means which estimates spectral characteristics of illumination based on the subspace information to be represented by the distribution characteristic selected by the dimension reduction means.

(Supplemental Note 2)

The illumination estimation device according to Supplemental Note 1, further including:

illumination information storage means which stores information representing parameters for use in configuring an illumination model, wherein the illumination estimation means estimates the spectral characteristics of the illumination based on the subspace information and the illumination model configured based on the information stored in the illumination information storage means.

(Supplemental Note 3)

The illumination estimation device according to Supplemental Note 1 or 2, wherein the distribution characteristics estimation means estimates a main component vector in a set of the observation values, as the distribution characteristics.

(Supplemental Note 4)

The illumination estimation device according to Supplemental Note 1 or 2, wherein the distribution characteristics estimation means estimates, as the distribution characteristics, vectors constituting the subspace, the subspace being obtained by approximating the distribution of the observation values in the spectral space as the subspace including an origin.

(Supplemental Note 5)

An illumination estimation method, including, by an information processing device:

extracting an object area from a multispectral image, the object area being an area, including specular reflection, of an object;

estimating information representing a subspace that approximates a distribution of observation values in a spectral space, as distribution characteristics, the distribution characteristics being characteristics of a spreading manner of the observation values in the object area within the spectral space;

selecting a distribution characteristic to be used from among the estimated distribution characteristics depending on the number of dimensions to be reduced, the number of dimensions to be reduced being determined in advance by a light environment; and estimating spectral characteristics of illumination based on the subspace information to be represented by the selected distribution characteristic.

(Supplemental Note 6)

The illumination estimation method according to Supplemental Note 5, wherein the information processing device stores in advance information representing parameters for use in configuring an illumination model, and the information processing device estimates the spectral characteristics of the illumination based on the subspace information and the illumination model configured based on the stored information.

(Supplemental Note 7)

The illumination estimation method according to Supplemental Note 5 or 6, wherein the information processing device estimates a main component vector in a set of the observation values, as the distribution characteristics.

(Supplemental Note 8)

The illumination estimation method according to Supplemental Note 5 or 6, wherein the information processing device estimates, as the distribution characteristics, vectors constituting the subspace, the subspace being obtained by approximating the distribution of the observation values in the spectral space as the subspace including an origin.

(Supplemental Note 9)

An illumination estimation program which causes a computer to execute:

a target object area extraction process of extracting an object area from a multispectral image, the object area being an area, including specular reflection, of an object;

a distribution characteristics estimation process of estimating information representing a subspace that approximates a distribution of observation values in a spectral space, as distribution characteristics, the distribution characteristics being characteristics of a spreading manner of the observation values in the object area within the spectral space;

a dimension reduction process of selecting a distribution characteristic to be used from among the distribution characteristics estimated in the distribution characteristics estimation process depending on the number of dimensions to be reduced, the number of dimensions to be reduced being determined in advance by a light environment; and an illumination estimation process of estimating spectral characteristics of illumination based on the subspace information to be represented by the distribution characteristic selected in the dimension reduction process.

(Supplemental Note 10)

The illumination estimation program according to Supplemental Note 9, wherein the program causes the computer comprising illumination information storage means which stores information representing parameters for use in configuring an illumination model to estimate the spectral characteristics of the illumination based on the subspace information and the illumination model configured based on the information stored in the illumination information storage means in the illumination estimation process.

(Supplemental Note 11)

The illumination estimation program according to Supplemental Note 9 or 10, wherein the program causes the computer to estimate a main component vector in a set of the observation values as the distribution characteristics in the distribution characteristics estimation process.

(Supplemental Note 12)

The illumination estimation program according to Supplemental Note 9 or 10, wherein the program causes the computer to estimate, as the distribution characteristics, vectors constituting the subspace to be obtained by approximating the distribution of the observation values in the spectral space as the subspace including an origin in the distribution characteristics estimation process.

The invention has been described as above referring to the exemplary embodiments. However, the invention of the present application is not limited to the aforementioned exemplary embodiments. The configuration and details of the invention may be modified in various ways comprehensible to a person skilled in the art in the scope of the invention.

This application claims the priority based on Japanese Patent Application No. 2013-128754 filed on Jun. 19, 2013, and all of the disclosure of which is hereby incorporated.

INDUSTRIAL APPLICABILITY

According to the invention, it is possible to estimate spectral characteristics of illumination at the time of capturing an image, only with use of the image as information at the time of capturing. Therefore, the invention is advantageously applicable for use in obtaining various pieces of information such as the kind, the material, and the state of an object within a multispectral image with use of the multispectral image with high precision, for instance.

REFERENCE SIGNS LIST 100, 200 Illumination estimation device
101 Image reading unit
102 Target object area extraction unit
103, 203 Distribution characteristics estimation unit
104, 204 Dimension reduction unit
105, 205 Illumination estimation unit
106 Illumination information storage unit
20 Image capturing device
30 Output device
501 Target object area extraction means
502 Distribution characteristics estimation means
503 Dimension reduction means
504 Illumination estimation means

What is claimed is:

1. An illumination estimation device, comprising:
a memory storing instructions; and
at least one processor configured to process the instructions to:
extract an object area from a multispectral image, the object area being an area, including specular reflection, of an object;
estimate information representing a subspace that approximates a distribution of observation values in a spectral space, as distribution characteristics, the distribution characteristics being characteristics of a spreading manner of the observation values in the object area within the spectral space;

select a distribution characteristic to be used from among the estimated distribution characteristics depending on the number of dimensions to be reduced, the number of dimensions to be reduced being determined in advance by a light environment; and estimate spectral characteristics of illumination based on the subspace information to be represented by the selected distribution characteristic.

2. The illumination estimation device according to claim 1, wherein:

the memory stores information representing parameters for use in configuring an illumination model, and the processor further configured to process the instructions to estimate the spectral characteristics of the illumination based on the subspace information and the illumination model configured based on the information stored in the memory.

3. The illumination estimation device according to claim 1, wherein the processor estimates a main component vector in a set of the observation values, as the distribution characteristics.

4. The illumination estimation device according to claim 1, wherein the processor, as the distribution characteristics, vectors constituting the subspace, the subspace being obtained by approximating the distribution of the observation values in the spectral space as the subspace including an origin.

5. An illumination estimation method, comprising:

extracting an object area from a multispectral image, the object area being an area, including specular reflection, of an object;

estimating information representing a subspace that approximates a distribution of observation values in a spectral space, as distribution characteristics, the distribution characteristics being characteristics of a spreading manner of the observation values in the object area within the spectral space;

selecting a distribution characteristic to be used from among the estimated distribution characteristics depending on the number of dimensions to be reduced, the number of dimensions to be reduced being determined in advance by a light environment; and estimating spectral characteristics of illumination based on the subspace information to be represented by the selected distribution characteristic.

6. The illumination estimation method according to claim 5, the method further comprising:

storing in advance information representing parameters for use in configuring an illumination model, and estimating the spectral characteristics of the illumination based on the subspace information and the illumination model configured based on the stored information.

7. The illumination estimation method according to claim 5, the method further comprising:

estimating a main component vector in a set of the observation values, as the distribution characteristics.

8. The illumination estimation method according to claim 5, the method further comprising:

estimating, as the distribution characteristics, vectors constituting the subspace, the subspace being obtained by approximating the distribution of the observation values in the spectral space as the subspace including an origin.

9. A non-transitory computer readable storage medium recording thereon a program, causing a computer to execute:

a processing of extracting an object area from a multispectral image, the object area being an area, including specular reflection, of an object;

a processing of estimating information representing a subspace that approximates a distribution of observation values in a spectral space, as distribution characteristics, the distribution characteristics being characteristics of a spreading manner of the observation values in the object area within the spectral space;

a processing of selecting a distribution characteristic to be used from among the distribution characteristics estimated in the processing of estimating the information depending on the number of dimensions to be reduced, the number of dimensions to be reduced being determined in advance by a light environment; and a processing of estimating spectral characteristics of illumination based on the subspace information to be represented by the distribution characteristic selected in the processing of selecting.

10. The non-transitory computer readable storage medium according to claim 9, wherein the program causes the computer comprising a illumination information storage unit which stores information representing parameters for use in configuring an illumination model to estimate the spectral characteristics of the illumination based on the subspace information and the illumination model configured based on the information stored in the illumination information storage unit in the illumination estimation process.

* * * * *